United States Patent [19]

Best

[11] Patent Number: 5,082,928
[45] Date of Patent: Jan. 21, 1992

[54] METHOD OF PREPARING CONJUGATED ANTIBODIES

[76] Inventor: Mark P. Best, 146 Caversham Valley Road, Dunedin, New Zealand

[21] Appl. No.: 434,484

[22] Filed: Nov. 13, 1989

Related U.S. Application Data

[63] Continuation of Ser. No. 875,093, Jun. 17, 1986, abandoned.

[30] Foreign Application Priority Data

Jun. 17, 1985 [NZ] New Zealand ............ 212437

[51] Int. Cl.$^5$ .................... C07K 3/06; A61K 39/00
[52] U.S. Cl. .................... 530/389; 530/390; 530/391; 530/413; 424/1.1; 424/85.91; 436/541; 436/804
[58] Field of Search ........... 530/389, 390, 391, 413; 424/85.91, 1.1; 436/541, 804

[56] References Cited

U.S. PATENT DOCUMENTS

| | | | |
|---|---|---|---|
| 4,460,559 | 7/1984 | Goldenberg | 424/1.1 |
| 4,658,022 | 4/1987 | Knowles et al. | 530/395 |

OTHER PUBLICATIONS

Garnett et al., Cancer Res. 46, 1986, pp. 2407-2412.
Kennedy et al., Chinica Chimica Acta 70, 1976, pp. 1-31.
Mark P. Best, Aust. J. Chem., 1982, 35, 2371-75.
Tian Yow Tsong, Biochemistry, vol. 14, No. 7, 1975, p. 1542.
M. Horowitz et al., Journal of Nuclear Medicine, vol. 26, No. 5, p. 46, 1985.
Peter Liu et al., The Journal of Nuclear Medicine, p. 28, vol. 26, No. 5, May 1985.
Allan H. Gobuty et al., Journal of Nuclear Medicine, vol. 26, No. 5, May 1985.
C. H. Paik et al., The Journal of Nuclear Medicine, vol. 24 (10), 1983.
Kaiser, Science, Dec. 7, 1984, vol. 225, No. 4679.
M. P. Best, Jnl. of Nuclear Medicine 25, p. 18 (1984) (Abstr.).

Primary Examiner—F. T. Moezie
Assistant Examiner—Andrew G. Rozycki
Attorney, Agent, or Firm—Birch, Stewart, Kolasch & Birch

[57] ABSTRACT

The present invention is directed to a method of preparing a conjugated antibody agent, and conjugated antibody agent obtained thereby. The method includes:
(i) attaching a substantially pure antigen to a solid phase;
(ii) passing an antibody containing composition over the solid phase such that the antibody is caused to bind to the attached antigen by immunoreaction to form a bound antigen-antibody complex;
(iii) passing a reactive conjugating agent over the bound antigen-antibody complex to conjugate the conjugating agent to said complex; to
(iv) removing the resultant conjugated antibody from the solid phase.

11 Claims, 3 Drawing Sheets

FIG. I

SOLID PHASE ANTIBODY PROCESSING
AFFINITY CONJUGATION OF ANTI-CALCITONIN (MECHANISM)

IMMUNO-ADSORBENT BEAD PREPARATION

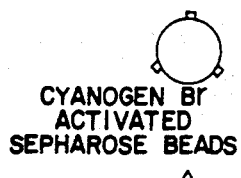

CYANOGEN Br ACTIVATED SEPHAROSE BEADS

1. SWELL AND WASH BEADS 0.001 M HCL 15 MINS
2. COUPLE Xmg CT HCO₃ BUFFER 2 HRS RT △
3. WASH 3X HCO₃ BUFFER
4. REACT 1 M ETHANOLAMINE PH 8 2 HRS RT
5. WASH 0.1 M ACETATE BUFFER pH 4 ⎫
6. WASH 0.1 M BORATE BUFFER pH 8 ⎬ 3X
7. INCUBATE IN ANTIBODY
8. WASH 3X PBS

CONJUGATION & ELUTION

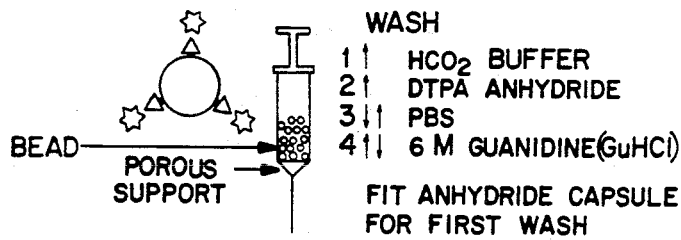

WASH
1. HCO₂ BUFFER
2. DTPA ANHYDRIDE
3. PBS
4. 6 M GUANIDINE (GuHCl)

FIT ANHYDRIDE CAPSULE FOR FIRST WASH

BEAD — POROUS SUPPORT

CALCITONIN ANTISERUM ASCITES FLUID

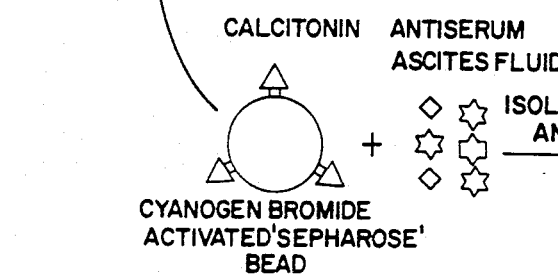

ISOLATION OF ANTI CT

CYANOGEN BROMIDE ACTIVATED 'SEPHAROSE' BEAD

DTPA CONJUGATION

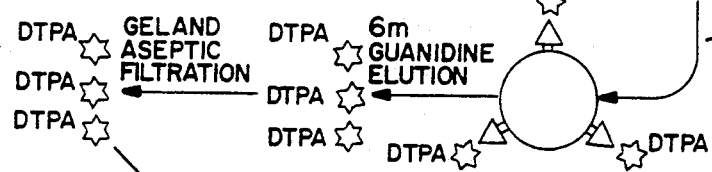

DTPA GEL AND ASEPTIC FILTRATION ← DTPA 6m GUANIDINE ELUTION

RENATURATION

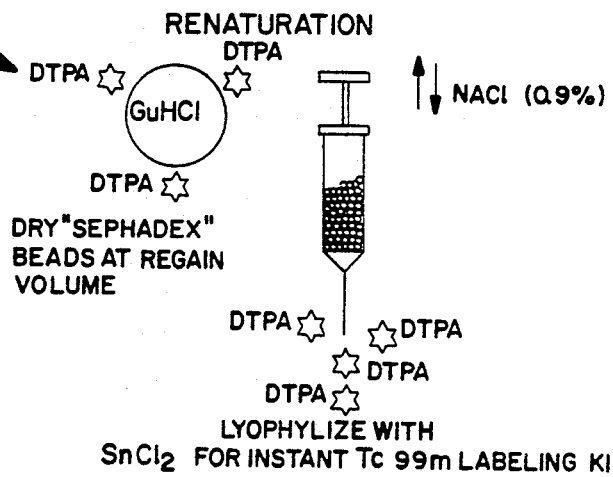

DRY "SEPHADEX" BEADS AT REGAIN VOLUME

↕ NaCl (0.9%)

LYOPHYLIZE WITH SnCl₂ FOR INSTANT Tc 99m LABELING KIT

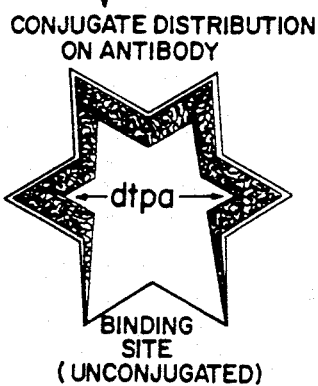

CONJUGATE DISTRIBUTION ON ANTIBODY

←dtpa→

BINDING SITE (UNCONJUGATED)

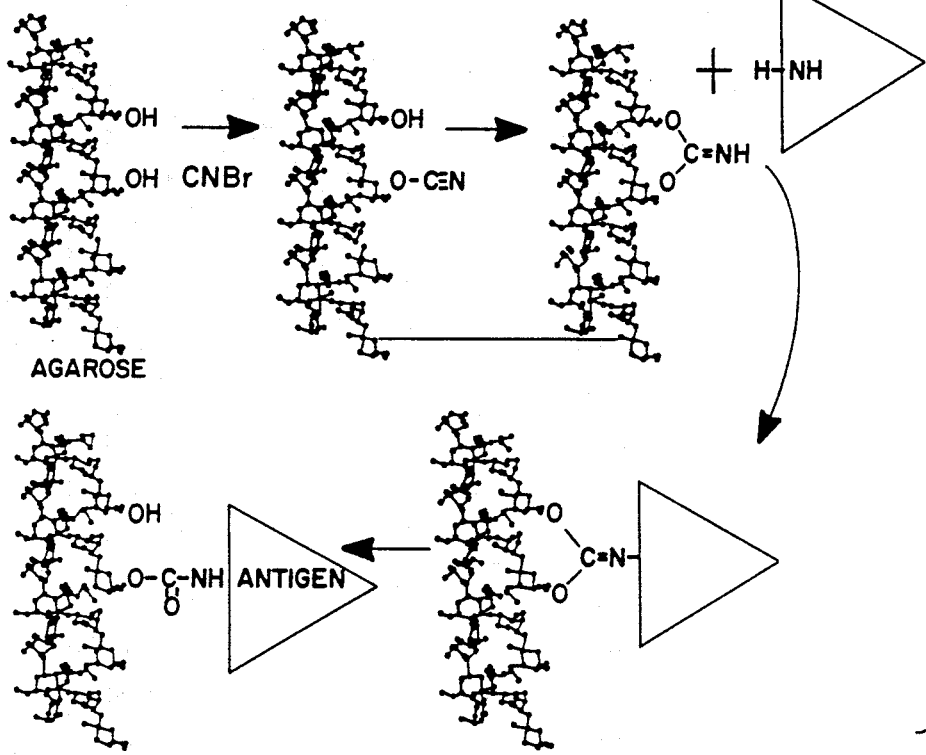

FIG. 4
SITE DIRECTED BOLTON HUNTER CONJUGATION PATHWAY FOR IODINATION OF ANTIBODY RETAINING HIGH IMMUNOREACTIVITY
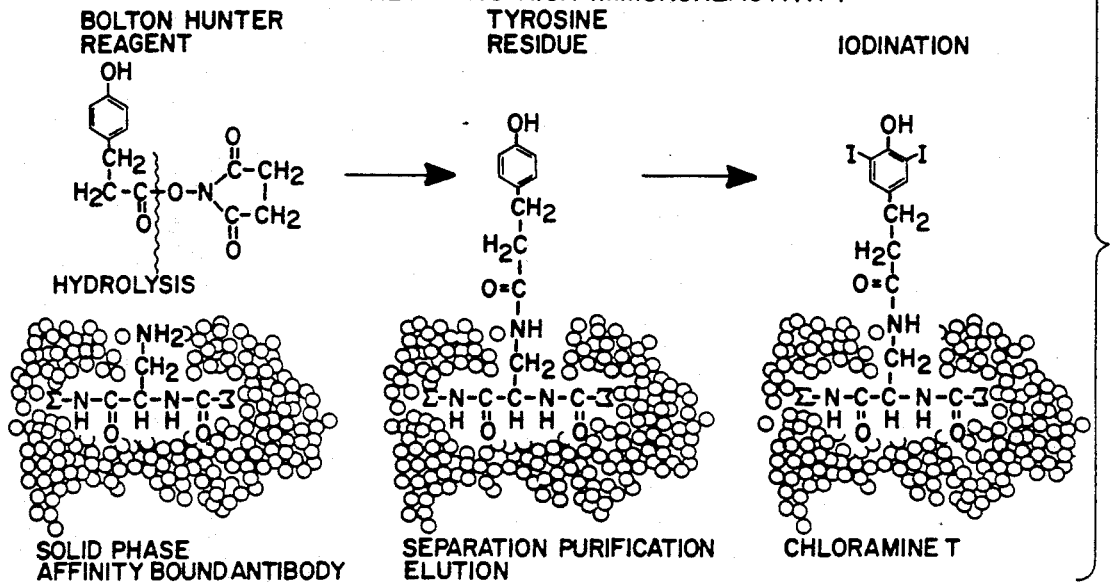
FIG. 5
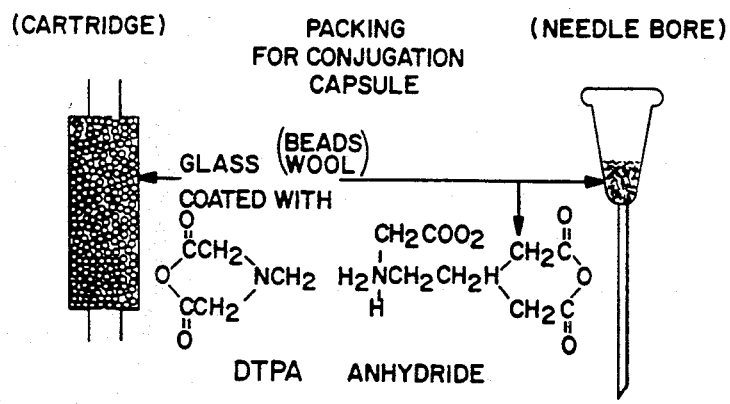
FIG. 6
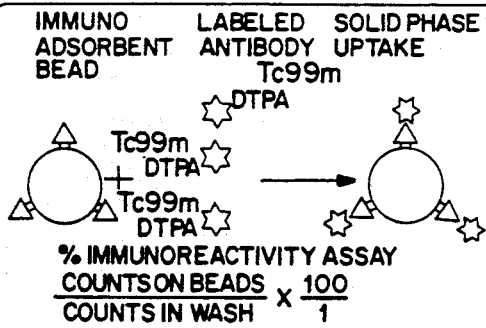
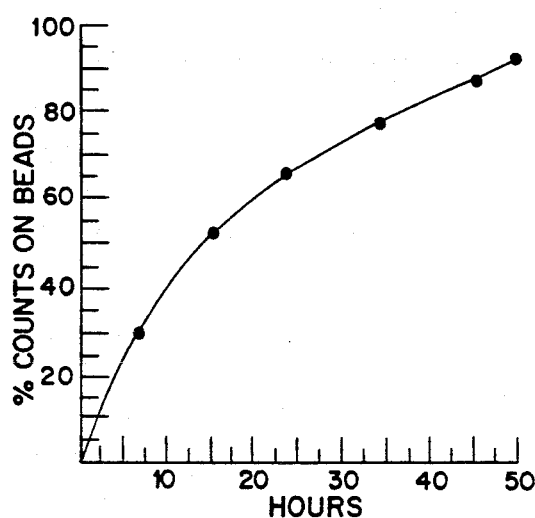

METHOD OF PREPARING CONJUGATED ANTIBODIES

This application is a continuation of application Ser. No. 06/875,093 filed on Jun. 17, 1986, now abandoned.

This invention relates to a Site-directed highly conjugated agent, particularly a radio labelled agent for use in clinical immunoscintigraphic studies. It has been a goal to site-direct and increase the number of substituents per antibody molecule without impairing native immunoreactivity (See Gobuty, A. et al Radiolabelled Monoclonal Antibodies: Radiochemical Pharmacokinetic and Clinical Challenges, J. Nuc. Med. Vol. 26, No. 5 546–47 1985.

High specific labelling is desirable to allow smaller quantities of antibody or fragments thereof to be economically provided for scintigraphy and therapy. The highly conjugated antibody agent is suitable for instant labelling by traditional labelling methodology, e.g., Instant Technetium 99m labelling Stannous kits; as used routinely in many nuclear medicine procedures.

Radiolabelling for immunoscintigraphy and therapy, and paramagnetic labelling for nuclear magnetic resonance imaging can be achieved with minimal disruption of the antibody's biological activity of binding to its specific antigen in the present invention.

While such scintigraphic studies are particularly useful in the detection of tumors and this use will be emphasized in the description hereinafter, it is to be appreciated that the present invention can be used wherever antigens are present and can be reacted with the radio labelled antibodies contained in the agent of the present invention so that the antigens can thereby be detected, e.g., Infarct Size Imaging by Tc 99m Labelled Antimyosin Antibody J. Nuc. Med. Vol. 26 No. 5, P28 May 1985 Liu et al.

The use of aerosol delivered radio labelled antibodies to ectopic lung carcinoma antigens in scintigraphic tumor detection is described in J. Nuc. Med. 25 P18 1984 (M. P. Best) while lung imaging with radio labelled agents is described and claimed in my New Zealand patent specification 203949. Also an improved method of calculating aerosol droplets dimensions suitable for use in aerosol delivery of the radio labelled antibodies is described in my New Zealand patent specification 208274.

To the present time however, the labelling of antibodies for immunoscintigraphic imaging can be inefficient due to the labelling of impurities present with the antibody preparation. Although this problem has been largely overcome with the availability now of synthetic antigens prepared in very pure form (e.g. peptide fragments, and monoclonal separation and culture technology), purification may still be necessary. However, there remain the problems with inertness of the antibody to labelling, and the antibody-binding site being conjugated (if conjugation is used during the preparation of the labelled antibody agent), in attempting to improve the labelling efficiency, with in vivo label stability, and with low antigen-antibody reaction after labelling. Existing conjugation methods permit only up to 60% efficiency.

It is thus an object of the present invention to provide a method of preparing a highly conjugated antibody agent which term herein includes a lymphocyte and an improved labelled antibody agent which will overcome or at least obviate disadvantages associated with such agents and methods of preparing the same to the present time.

Further objects of this invention will become apparent from the following description.

According to one aspect of the present invention there is thus provided a method of preparing a highly conjugated antibody agent comprising:
1. Attaching a substantially pure antigen to a solid phase;
2. Passing an antibody-containing composition over said solid phase such that the antibody binds to said attached antigen, by immunoreaction;
3. Passing a reactive conjugating agent over bound antibody-antigen complex to conjugate said agent to said complex;
4. Removing the antibody-chelate conjugate from said solid phase.

According to a further aspect of this invention, there is provided a labelled antibody agent for use in clinical scintigraphic study, said agent comprising an antibody-chelate conjugate having its antigen-binding sites substantially free from conjugated chelate.

According to a still further aspect of the invention, there is provided a method of preparing a labelled antibody agent substantially as herein described.

According to a still further aspect of the invention, there is provided a labelled antibody agent prepared by the methods as herein described.

It will be appreciated that said highly conjugated antibody may be linked to a variety of other agents as desired. It is anticipated that radiolabelling agents will be particularly utilized, and also agents visible by nuclear magnetic resonance ("NMR" herein) scanning, such as Gadolinium.

In addition, cytotoxic substances may similarly be linked to said agent.

Additionally, combinations of agents may be linked either directly to the agent or through each other.

Further, the conjugating agent may be inherently therapeutic, for example, cytotoxic residues of methotrexate and ricin. The appropriate ester or anhydride hydrolysis for the solid phase bead complex is performed. The site directed conjugate will target the cytotoxic therapy while minimizing adverse toxicity, as it will be localized by the specificity of the site directed antibody.

More specifically, the present invention is directed to a method of preparing a conjugated antibody agent comprising the steps of
(I) (a) packing Sepharose ® beads in the column of a syringe;
(b) washing said solid phase with 0.001M HCl for 15 minutes;
(c) coupling calcitonin $HCO_3-$ buffer for two hours at room temperature;
(d) washing the column with $HCO_3-$ buffer three times;
(e) reacting said beads with 1M ethanolamine at about pH 8 for 2 hours at room temperature;
(f) washing said beads with 0.01M acetate buffer at about pH 4;
(g) washing said beads with 0.01M borate buffer at about pH 8;
(h) repeating said steps (f) and (g) three times;
(i) washing said column with an antibody containing solution;
(j) washing said column with phosphate buffered saline to form an immuno-adsorbent bead complex being solid phase cyanogen bromide activated beads covalently linked to a bound antibody;

(II) conjugating said immuno-adsorbent bead complex with a coupling agent to form a conjugated antibody by
   (a) washing said column with an $HCO_3-$ buffer;
   (b) flushing said column with diethyamine triamine pentacetic acid anhydride;
   (c) washing said column with phosphate buffered saline;
   (d) eluting said antibody chelate conjugate with 6M guanidine HCl, and (III) separating said antibody chelated conjugated from said guanidine HCl by instant gel filtration.

The present invention will now be described by way of examples and with general reference to the aforementioned Figures.

BRIEF DESCRIPTION OF THE DRAWINGS

FIG. 1 is a general diagram of a method of preparing a conjugated antibody according to the invention.

FIG. 2 is a diagram of cyanogen bromide activation and attachment of an antigen to a solid phase according to the invention.

FIG. 3 is a diagram of the methodology of conjugation of a conjugating agent to an antibody-antigen complex and elution of the resultant conjugated-antibody.

FIG. 4 is a diagram of a site directed Bolton Hunter conjugation pathway for Iodination of Antibody retaining high immunoreactivity.

FIG. 5 is a diagram of showing packing of conjugation capsules.

FIG. 6 is a diagram showing a % immunoreactivity wherein % counts on beads is plotted against time.

The present invention will now be described by way of example and with reference to possible embodiments thereof, and with particular reference to the accompanying FIG. 1 which shows respectively possible procedures in (a) affinity conjugation, (b) renaturation, (c) affinity conjugation of DTPA-anticalcitonin, and (d) immuno-absorbent bead preparation.

In one possible process for the preparation of an affinity conjugated antibody and fragments for instant labelling with for example Technetium 99m for use in clinical immunoscintigraphic studies, the process may provide for the packing of immunoadsorbent beads in a syringe or other column. This will allow small volume sequential solid phase processing with liquid reagents to effect high selection efficiency, fragmentation, conjugation, and labelling of sensitive immunoglobulin antibodies particularly those useful in biologically specific immunoscintigraphic imaging of occult cancer with a gamma camera, or nuclear magnetic N.M.R. techniques and therapeutic applications.

The labelled antibody so provided will then be able to react specifically at tumor or other antigen sites with a tumor or other type associated antigen.

It is to be appreciated that many antibodies with a variety of biologically reactive antigens are being researched at the present time throughout the world in order to provide for early non-invasive cancer detection. Immunoreactive lymphocytes can thus also be conjugated in this system which will result in site directed labelling for maximum immunoreactivity.

A scintigraphic image created by immunoreaction at a tumor site of a radio labelled antibody with the associated tumor antigen can provide detailed particulars of the tumor from the image so formed.

While the use of radio labelled antibodies has been previously proposed in respect of the ventilation route, for example in J. Nucl. Med. 25 P18 1984 (M. P. Best), it is mentioned that the present invention is not restricted thereto but can be used for example also in the traditional intravenous route. Calcitonin antibodies used intravenously instead of by ventilation to detect ectopic calcitonin production of tumors is appealing due to contrast enhancement by background clearance with the thyroid concentration of calcitonin in normal physiological endocrinology.

Synthetic antigens can be prepared in very pure form such as by solid phase peptide synthesis as developed originally by Merrifield which won the Nobel Prize in Chemistry in 1984 and as described in Science, Vol. 226, No. 4679, December 1984.

Peptide synthesis enables antigenic epitopes to be synthesized and utilized in the solid phase methodology enabling very specific antibodies to be processed, e.g., bioactive peptide fragments such as the human chorionic gonadotrophin beta chain.

Many products of this synthesis are now available commercially such as calcitonin, bombesin and ACTH. These antigens are also well documented tumor associated antigens. Specific selection by an antibody-antigen reactivity is in the present invention utilized to isolate pure antibody on to immunoadsorbent solid phase material, suitably beads packed in a column in a syringe as mentioned above. In a process of the present invention, sequential washing with appropriate reagents may allow the aforesaid immunoadsorbent beads to be prepared. One of the Figures of the accompanying drawings illustrates one such method of preparation of suitable immunoadsorbent agarose beads, while in FIG. 1 is shown, inter alia, the use of Sepharose ® (trade mark) beads.

The antigen may be attached covalently to the solid phase material using for example cyanogen activated Sepharose ® 6MB (trade mark) beads, available commercially, packed in a syringe for example. (Epoxy activated-Sepharose beads can also be used). The exclusion limit of the beads is $4 \times 10$ Daltons thus immunoreactive lymphocytes can also be conjugated in this way. Sepharose with its macroporosity specifications from its open pore structure, its availability as beads with a large bed volume and its favorable fractionation range as utilized in gel filtration is suitable for the solid phase adsorbent. Immunospecific lymphocytes with binding sites on the cell surface can thus also be conjugated to provide high specific labelling while maintaining immunoreactivity. These immunoadsorbent beads may then be washed and solution containing antibody to be isolated may be passed over the beads and then may be washed for example with a salt solution. These beads can be used to test immunoreactivity of the labelled conjugate, e.g., quantitatively, xMBq of Tc 99m-antibody conjugate is incubated with a sample of the adsorbent beads: -% x megabequerels found on beads and % MBq found in work gives % immunoreactivity as an assay. This and a plot of resulting data are shown in FIG. 6.

It has been found that both monoclonal and polyclonal antibody preparations may require purification so that only the specific antibody is ultimately labelled. As mentioned above, this has been a considerable problem in the past without a consistently pure characterized antigen, which minimizes cross reactivating.

Specific biological antibody-antigen affinity as a method of purification may preferably be used but other non-specific methods are possible, such as clonal separations and HPLC.

Monoclonal antibodies available pure from clonal separation technology sometimes require an impure adsorbent to effect immunoaffinity as the corresponding antigent may not be completely characterized or may be difficult to isolate. Specific antigen bound to the solid phase can be from tumor extracts for example, for tumor specific antibody adsorption. A low level of impurity is acceptable provided that it is firmly attached to the solid phase. Tandem antibody "cocktails" can be also processed using the solid phase process depending on immunoadsorbent specificity. Conjugation and elution, and renaturation are shown diagrammatically in FIG. 3.

Direct labelling with Technetium using stannous chloride reduction is a method used in the past commonly to attach the carrier. However, it is very inefficient requiring post labelling purification, e.g., Sephadex filtration and often the binding site is labelled rendering the antibody non immunoreactive. Reported immunoreactivity ranges from 40%–60% with the remaining non-specific agent raising the background severely affecting contrast, resolution and clinical value of the images and giving adverse toxicity in the case of therapy.

Most carriers used clinically will not be affected in this way, e.g., Tc99m phosphates used in bone scanning. However, in the present invention, conjugation is used to improve labelling efficiency and reactivity can be increased to over 75% and possibly over 90%. Conjugation is so arranged in the present invention so as to couple a relatively large number of reactive groups on to the antibody and the labelling means such as Technetium can be attached to the coupling moiety. The coupling moiety may be diethylenetriamine pentacetic acid (DTPA) (See Paik CH et al, Journal of Nuclear Medicine 24: 932-936, 1983) and desferrioxamine or iminodiacetic acid can also be used, for example. Iminodiacetic acid conjugation is possible using nitrilotriocetic acid monoanhydride. Aust. J. Chem., 1982, 35, 2371-5, Best et al. Thus, a gamma emitting isotope Tc-99m, indium 111 and paramagnetic contrast agent such as gadolinium may be attached with high specificity to the immunoreactive agent while maintaining immunoreactivity. DTPA conjugates can be used for Technetium labelling via stannous chloride, indium 111 labelling via transchelation, e.g., indium citrate or acetate. Therapeutic immunoreactive agents yttrium 90 and palladium can also be attached to DTPA conjugates. Bolton Hunter Reagent (3-(p-Hydroxyphenyl) propionic acid N-Hydroxysuccinimide ester, Sigma H1256 Sigma Chemical Company, P.O. Box 14508, St. Louis, Mo.) is an activated ester which hydrolyses to produce a tyrosine residue which will couple with protein amine groups. It can be applied to the solid phase methodology to produce a highly conjugated immunoreactive agent and it can be subsequently iodinated with iodine via chloramine T to attach iodine 123, 125 or 131 as shown in FIG. 4 for diagnosis and therapy as above.

The present invention utilizes conjugation with the antibody attached to the solid phase immunoadsorbent material such as beads allowing coupling reagents to be removed after the reaction and the antibody conjugate to be washed. In the solid phase, attachment of the present invention, the antibody binding site involved with antigen-antibody bond is inaccessible and is protected from being conjugated. Accordingly, conjugation will substantially take place only in reactions in non-binding sites. By conjugating the coupling moiety to an antibody in an existing bound state with its associated antigen, greater amounts of the coupling moiety may be attached without impairing antibody-antigen reactions in vitro or in vivo. Only very small amounts of DTPA conjugate can be applied without immunoreactive damage using a conventional homophasic aqueous reaction system. (0.7 DTPA molecules for one molecule of antibody.) (See Horowitz et al, Journal of Nuclear Medicine, Vol. 26, No. 5, P46, 1985). With an increased amount of attached coupling moiety, greater amounts of labelling material may be coupled to the antibody for improved scintigraphic imaging.

Conjugation utilizes an anhydride capsule to deliver DTPA anhydride and a high conjugate to antibody ratio is obtained. DTPA anhydride is unstable in water and the capsule in the form of a cartridge or needle bore is attached to the syringe column for the first washing in the conjugation sequence. A capsule with a suitable dose of anhydride is prepared by dissolving DTPA anhydride (available commercially) and coating beads or a porous support (as in diagram) and evaporating the solvent. This is shown diagrammatically in FIG. 5.

Elution of antibody conjugate by increasing the ionic strength with 6 Molar Guanidine HCL solution may be used to cleave conjugated antibody from the immunoadsorbent beads or the like. Biological perturbance is manifested by an unfolding of the antibody disrupting hydrogen bonding and the antibody is displaced into the liquid phase effecting separation. The electrostatic antibody-antigen bond may be disrupted to effect cleavage and the antibody conjugate may be separated into the wash. Guanidine hydrochloride and urea salts react with water inducing a conformational transition effecting folding of both the antibody and antigen with resultant elution and separation into the aqueous phase. (See Tsong T. Y. An acid induced conformational transition of denatured cytochrome C in urea and quanidine hydrochloride solutions Biochemistry, Vol. 14, No. 7, 1542-47, 1975). The conjugated immunoreactive agent can be separated by biological perturbance from the bead complex otherwise non specifically conjugated. The aforementioned conjugation is diagrammatically illustrated in FIG. 1.

In the renaturation, again shown very diagrammatically in FIGS. 1 and 3, the antibody conjugate can be renatured virtually instantaneously by gel filtration into dry Sephadex ® (trade mark) beads packed in a suitable syringe for example. The aforesaid beads swell and the guanidine HCL may be filtered out. The antibody conjugate can be washed and separation into isotonic salt solution results in renatured immunoreactivity. Dialysis can also be used. This conjugate may be mixed with a small amount of stannous chloride and lyophylized to form a required instant labelling kit. For labelling, up to for example 50 millicuries (18GBq) TcO$_4$ may be added. A high percentage of immunoreactivity will be maintained as the labelling means is preferentially attached to the conjugating moiety preferentially coupled to the non-binding sites. The technetium 99m (TcO$_4$) solution may be produced from commercially available Technetium generators as utilized with instant labelling of a wide variety of radiopharmaceuticals in the majority of nuclear medicine imaging procedures. The radiopharmaceutical kit of a preferred embodiment of the present invention will contain conjugated antibody and stannous chloride which is aseptically sterilized by filtration, lyophylized and sealed in a glass vial and will, it is believed, to be useable for over 6 months if refrigerated.

As it will be clear from the above, the method of the present invention can provide an instant labelling kit which can provide a high, possibly more than 90% labelling efficiency with no post labelling procedures, to produce in the example mentioned above a technetium-antibody chelate with a high level of immunoreactivity. The method of preparation thereof is relatively non-complex and readily performed with solid phase synthetic methodology such as described.

Where in the aforegoing description reference has been made to specific components or integers of the invention having known equivalents then in such equivalents are herein incorporated as if individually set forth.

Although this invention has been described by way of example and with reference to the possible embodiments thereof it is to be understood that modifications or improvements may be made thereto without departing from the scope or spirit of the invention.

What we claim is:

1. A method of preparing a conjugated antibody comprising
   (i) attaching a substantially pure antigen to a solid phase;
   (ii) passing an antibody containing composition over said solid phase such that said antibody binds to said attached antigen to form a bound antigen-antibody complex;
   (iii) passing a reactive chelating agent over said bound antigen-antibody complex to chelating said conjugating agent to said complex; and
   (iv) removing the resultant conjugated antibody from said solid phase.

2. A method of preparing a conjugated antibody comprising:
   (i) reacting a substantially pure antigen with an antibody to form a bond antigen-antibody complex;
   (ii) conjugating a reactive chelating agent with said bound antigen-antibody complex; and
   (iii) cleaving said antigen from said antibody to form a conjugated antibody.

3. A method of preparing a conjugated antibody comprising the steps of
   (I) (a) packing a solid phase in the column of a syringe;
   (b) washing said solid phase with 0.001M HCl;
   (c) coupling calcitonin $HCO_3-$ buffer for two hours at room temperature;
   (d) washing the column with $HCO_3-$ buffer;
   (e) reacting said beads with 1M ethanolamine at about pH 8;
   (f) washing said beads with 0.1M acetate buffer at about pH 4;
   (g) washing said beads with 0.1M borate buffer at about pH 8;
   (h) repeating said steps (f) and (g);
   (i) washing said column with an affinity antibody containing solution;
   (j) washing said column with phosphate buffered saline to form an immuno-adsorbent bead complex with said antibody;
   (II) conjugating said immuno-adsorbent bead complex with a chelating agent to form a conjugated antibody by
   (a) washing said column with an $HCO_3-$ buffer;
   (b) flushing said column with diethylamine triamine pentacetic acid anhydride;
   (c) washing said column with phosphate buffered saline;
   (d) eluting said antibody chelate conjugate with 6M guanidine HCl; and
   (III) separating said antibody conjugate from said guanidine HCl by gel filtration.

4. The method of claim 1 further comprising labelling said conjugated antibody with a labelling agent selected from the group consisting of a radio-labelling agent and a NMR scanning contrast agent.

5. The method of claim 1 further comprising labelling said conjugated antibody by mixing same with stannous chloride, lyophilizing and adding radio-labelling agent.

6. A method as claimed in claim 5 in which the radio-labelling agent is technetium.

7. A method of preparing site directed cytotoxic or therapeutic agents comprising the additional subsequent step of conjugating a cytotoxic or therapeutic agent with the conjugated antibody prepared according to the method of claim 1.

8. The method according to claim 7 wherein said therapeutic agent is selected from the group consisting of yttrium 90, palladium, methotrexate, ricin and iodine.

9. The method according to claim 7 wherein said cytotoxic agent is selected from the group consisting of methotrexate and ricin.

10. A method as claimed in claim 1 in which said chelating agent is selected from the group consisting of DTPA, iminodiacetic acid, and desferrioxamine.

11. A method as claimed in claim 1 in which said antigen is a tumour associated antigens.

* * * * *